(12) United States Patent
Kompothecras et al.

(10) Patent No.: US 11,865,107 B2
(45) Date of Patent: Jan. 9, 2024

(54) PHARMACEUTICAL COMPOSITION

(71) Applicant: Asclepius Pharmaceutical, LLC, Sarasota, FL (US)

(72) Inventors: Gary Kompothecras, Sarasota, FL (US); Michael Mullan, Sarasota, FL (US); Daniel Paris, Sarasota, FL (US)

( * ) Notice: Subject to any disclaimer, the term of this patent is extended or adjusted under 35 U.S.C. 154(b) by 0 days.

(21) Appl. No.: 17/009,960

(22) Filed: Sep. 2, 2020

(65) Prior Publication Data

US 2021/0052559 A1    Feb. 25, 2021

Related U.S. Application Data

(63) Continuation-in-part of application No. 16/602,690, filed on Nov. 20, 2019, now abandoned.

(60) Provisional application No. 62/917,129, filed on Nov. 21, 2018.

(51) Int. Cl.
| | | |
|---|---|---|
| A61K 31/4375 | (2006.01) |
| A61K 9/48 | (2006.01) |
| A61K 47/46 | (2006.01) |
| A61K 47/36 | (2006.01) |
| A61K 31/4355 | (2006.01) |
| A61K 9/00 | (2006.01) |
| A61K 36/9066 | (2006.01) |
| A61K 36/21 | (2006.01) |
| A61K 36/54 | (2006.01) |
| A61K 47/22 | (2006.01) |

(52) U.S. Cl.
CPC ........ *A61K 31/4375* (2013.01); *A61K 9/0014* (2013.01); *A61K 9/48* (2013.01); *A61K 31/4355* (2013.01); *A61K 36/21* (2013.01); *A61K 36/54* (2013.01); *A61K 36/9066* (2013.01); *A61K 47/22* (2013.01); *A61K 47/36* (2013.01); *A61K 47/46* (2013.01)

(58) Field of Classification Search
CPC .. A61K 31/4355; A61K 31/4375; A61K 9/68; A61K 9/0014
See application file for complete search history.

(56) References Cited

U.S. PATENT DOCUMENTS 8,283,135 B2 * 10/2012 Doyle ............... A61P 29/00
                                                      435/49
8,496,975 B2 *  7/2013 Bombardelli ....... A61P 31/10
                                                      424/725

\* cited by examiner

*Primary Examiner* — Kevin E Weddington

(57) ABSTRACT

A composition comprising a therapeutically effective amount of at least one alkaloid combined with one or more non-alkaloid components, wherein the composition is configured to be administered to a subject.

15 Claims, No Drawings

PHARMACEUTICAL COMPOSITION

CROSS-REFERENCE TO RELATED APPLICATION(S)

The present application claims priority to U.S. Non-Provisional patent application Ser. No. 16/602,690 filed on Nov. 20, 2019, entitled "ORALLY ADMINISTERED THERAPEUTIC COMPOSITION" the entire disclosure of which is incorporated by reference herein.

BACKGROUND

Field

The present disclosure relates to therapeutically effective pharmaceutical compounds. More particularly the present disclosure relates to therapeutically applicable pharmaceutical compositions incorporating one or more for the treatment of one or more diseases or conditions.

Description of the Related Art

Therapeutically effective compounds and compositions are generally developed through chemical processes combining one or more molecules of a known or desired physiological response. The combined molecules are often synthesized or derived from a natural source and evaluated for their therapeutic potential.

Certain categories of these molecules are formed based on similar response to their administration. For example, non-steroidal anti-inflammatory drugs (NSAID) can be considered a category of compounds that have a similar effect on the transmission of nerve signal transduction in response to inflammation-mediated conditions or diseases. Another categorical example of biologically active molecules are plant-derived alkaloids.

Plants represent a diverse taxonomic group of organisms that form alkaloids as a part of their growth and development. While often necessary to the plant, these alkaloids often have significant impact on mammalian cells. Whether it is anti-inflammatory and anti-oxidant in healthy cells or anti-tumoral and pro-apoptotic in malignant tissue, plant-based alkaloids provide a significant opportunity in pharmaceutical development in all diseases and conditions.

Many compounds have been derived from plants and extracted for their therapeutic potential. Extraction of a target compound is preferred to consumption of the entire plant or relevant parts as there may be undesired or harmful compounds within the total plant. Also, the effective concentration of these compounds may require that the extracts be consolidated at quantities that would impractical to achieve through consumption of the total plant.

However, therapeutic potential and cellular response is based on complex pathways and relevant feedback loops both intracellularly and extracellularly. The state of a cell is dynamic as it is an inherent characteristic of every cell to maintain equilibrium and carryout cellular functions. Accordingly, therapeutic compounds often require multi-functional and multifaceted impact to ensure the most effective desired physiological response. Therefore, a composition of molecules is often beneficial over single compounds as the composition offers increased or synergistic therapeutic results.

SUMMARY

Some embodiments disclosed herein provide a composition comprising a therapeutically effective amount of at least one alkaloid combined with one or more non-alkaloid components, wherein the composition is configured to be administered to a subject. In some embodiments, the composition formulation is a homogenous combination of at least one components described herein. The formulation may be manufactured using one or more chemical processes for compounding pharmaceutical compositions. The manufacturing process may involve conversion of the one or more components from a solid to a liquid or a liquid to a solid. In some embodiments, one or more of the components may be incorporated into the composition as a salt or salt derivative.

Some embodiments disclosed herein provide a composition comprising having at least one alkaloid is selected from the group consisting essentially of berberine, allocryptopine, alpha-homochelidonine, beta-homochelidonine, chelidonine, chelerythrine, coptisine, magnoflorine, protopine, sparteine, chelamine, and sanguinaria. Additional natural, synthetically manufactured, or bioequivalent components may be included in the composition. In some embodiments, the components described herein may be included into the composition after extraction from a natural source or synthesized. In some embodiments, the component may be extracted from a plant. In some embodiments, a portion of the plant is incorporated into the composition. In some embodiments, the alkaloid may be an active ingredient and selected based on the biological impact of the subject.

Some embodiments disclosed herein provide a composition comprising having at least one component selected from the group consisting essentially of allocryptopine, chelamine, chelidonine, chelerythin, coptisine, magnoflorine, protopine, sparteine, alpha-homochelidonine, beta-homochelidonine, chelidonic acid, malic acid, and citric acid. In some embodiments non-alkaloid components may be an active ingredient and selected based on the biological impact. In some embodiments the non-alkaloid component enhances a biological impact of an alkaloid component in the composition. In some embodiments, the non-alkaloid component may be included to increase or enhance metabolism of the composition by the subject.

Some embodiments disclosed herein provide a composition having a polyphenol. In some embodiments, the composition has one or more polyphenols. In some embodiments, the composition has one or more flavonoids and the polyphenol or the flavonoid may be an active ingredient selected for an intended biological response by the subject.

In some embodiments, the composition results in a biological or physiological response in the subject after the composition has been administered to the subject.

Some embodiments disclosed herein provide a composition having at least berberine. In some embodiments, berberine is at least one active ingredient in the composition. The composition having berberine may be administered to a subject and the berberine contacts tissue, cells, or other structure of the subject. In some embodiments, the subject has a physiological response to berberine or a berberine metabolite. In some embodiments, the composition comprises at least one alkaloid or non-alkaloid component in a therapeutically effective amount by weight of the included component Some embodiments disclosed herein provide a composition formulated to be orally administered.

Some embodiments disclosed herein provide a composition that is administered to a mammal. In some embodiments, the mammal is a human subject. In some embodiments, the mammal is a canine or feline and administration may include a formulation configured to be incorporated into the chow of the mammal. In some embodiments, the subject is a eukaryotic organism. In some embodiments, non-limiting examples of the subject are a cow, pig, horse, goat, chicken, rabbit, sheep, cattle, fish, duck, turkey, deer, buffalo, Some embodiments disclosed herein provide a composition having a therapeutically effective amount of one or more components based on a desired biological response of a subject to which the composition is administered.

Some embodiments disclosed herein provide a composition having at least 50 mg of berberine, 50 mg of beetroot, 20 mg of cinnamon, 25 mg of chondroitin and 25 mg of glucosamine. In some embodiments, the composition is formulated to be administered to a subject, wherein the subject is in need of the composition such that the composition improves, treats, prevents, or reduces a disease or condition of the subject.

Some embodiments disclosed herein provide a composition having at least 100 mg of berberine, 50 mg of chondroitin, 50 mg of glucosamine, 100 mg of beetroot powder, and 40 mg of turmeric.

Some embodiments disclosed herein provide a composition having at least 100 mg of berberine, 100 mg of beetroot, 1 mg of chelerythrine, and 40 mg of turmeric. In some embodiments, the therapeutically effective amount of the composition and included components is determined based on a dosage regiment. In some embodiments, the dosage regiment is a single dose. In some embodiments, the dosage regiment includes multiple and separate administration of the composition to the subject. In some embodiments, the dosage regiment includes increasing subsequent doses. In some embodiments, the dosage regiment involves a tapered dose.

Some embodiments disclosed herein provide a composition having at least one alkaloid is derived and extracted from a plant species.

Some embodiments disclosed herein provide a composition having at least one non-alkaloid excipient. Some embodiments disclosed herein provide a composition having one or more components configured to increase the bioavailability of the composition within the subject.

Some embodiments disclosed herein provide a composition configured to be administered topically to the subject. The formulation may be determined based on the attributes of the subject to which the composition is administered.

Some embodiments disclosed herein provide a composition having at least one alkaloid consists of berberine and chelerythrine. Some embodiments disclosed herein provide a composition having is at least chondroitin and glucosamine. Some embodiments disclosed herein provide a composition having at least curcumin.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "therapeutically effective amount" means an amount that is effective in therapy, or an amount sufficient to provide a therapeutic effect. An amount that is effective in therapy is an amount which produces a biological activity and will depend, among other things, on the individual.

The present disclosure may include reference to administration, application, or research involving one or more mammalian species. It is understood and contemplated that dosage conversions accepted and understood by a personal reasonably skilled in the art are applicable for the application of the composition to different species. The Food and Drug Administration provides guidance for the extrapolation of dosage across different species including, but not limited to, human equivalent doses based on body surface area. (FDA (2005), Guidance for Industry Estimating the Maximum Safe Starting Dose in Initial Clinical Trials for Therapeutics in Adult Healthy Volunteers).

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Composition

The present disclosure relates to a composition having at least one alkaloid in combination with one or more compounds for the purpose of treating or preventing a disease or condition in a living organism.

In some embodiments, the composition comprises multiple alkaloids selected based on the desired physiological response. For example, the composition comprises more than two alkaloids and may be combined with additional components, wherein the additional components may be alkaloids or non-alkaloids.

In some embodiments, the additional components may increase or enhance bioavailability, solubility, absorption, and/or pharmacokinetics.

In some embodiments, the composition is systematically absorbed and one or more metabolites of the composition constitute the therapeutically effective amount of the composition.

Alkaloids encompasses a large group organic compounds that contain nitrogen, generally positioned in a ring or cyclic structure of the alkaloid. Alkaloids can be sub-divided into different groups such as indoles, quinolines, isoquinolines, pyrrolidines, pyridines, pyrrolizidines, tropanes, and terpenoids and steroids based on their structure. Other subdivisions of alkaloids may be based on the plant species from which they are derived. While mainly derived from plants, alkaloids may be found and extracted from other organisms. Most alkaloids contain oxygen in their molecular structure & are usually colorless crystals at ambient conditions. Oxygen free alkaloids are volatile, colorless oily liquid eg. Nicotine; some alkaloids are colored eg. Berberine (yellow) and Sanguinarine (orange). Most alkaloids are weak bases but some of the alkaloids such as Theophylline are amphoteric. Many alkaloids dissolve poorly in water but readily dissolve in organic solvents Alkaloids forms salts of various strengths & these salts are usually soluble in water & ethanol and poorly soluble in most organic solvents. (Rajandeep Kaur et al.; Haya: Saudi J. Life Sci.; Vol-2, Iss-5 (August-September, 2017):158-189, the content of which is hereby incorporated by reference in its entirety).

In some embodiments, the at least one alkaloid is extracted from a source such as a plant or organism. Solvents and reagents may be used in combination with the alkaloid source to selectively dissolve the alkaloid for subsequent recovery from the solution.

Non-limiting examples of alkaloids include berberine, allocryptopine, alpha-homochelidonine, beta-homochelidonine, chelidonine, chelerythrine, coptisine, magnoflorine, protopine, sparteine, chelamine, sanguinaria, nicotine, strychnine, caffeine, morphine, pilocarpine, atropine, methamphetamine, mescaline, ephedrine, and tryptamine In some embodiments, the at least one alkaloid is combined with one or more flavonoids. Flavonoids are an important class of natural products; particularly, they belong to a class of plant secondary metabolites having a polyphenolic structure, widely found in fruits, vegetables and certain beverages. They have miscellaneous favorable biochemical and antioxidant effects associated with various diseases such as cancer, Alzheimer's disease (AD), atherosclerosis, etc.(1-3). Flavonoids are associated with a broad spectrum of health-promoting effects and are an indispensable component in a variety of nutraceutical, pharmaceutical, medicinal and cosmetic applications. This is because of their antioxidative, anti-inflammatory, anti-mutagenic and anti-carcinogenic properties coupled with their capacity to modulate key cellular enzyme functions. (Panche A N, Diwan A D, Chandra S R. Flavonoids: an overview. J Nutr Sci. 2016; 5:e47. Published 2016 Dec. 29. doi:10.1017/jns.2016.41, the content of which is hereby incorporated by reference in its entirety). A non-limiting example of the chemical formula for a flavonoid:

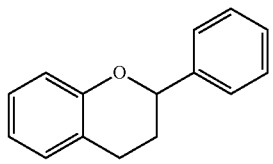 [SMILES: c1ccc(C2CCc3ccccc3O2)cc1]

Non-limiting examples of compounds combined with the at least one alkaloid in the composition include quercetin, chelidonic acid, malic acid, citric acid, *Chelidonium magus*, turmeric curcumin, beetroot, cinnamon, chondroitin sulfate, glucosamine sulfate, 1-carnitine, apigenin, *Chrysanthemum morifolium* extract (CME), hypromellose and silica.

Berberine

Berberine is a benzylisoquinoline alkaloid found in various plants such as *Berberis vulgaris, Berberis aristata, Mahonia aquifolium, Hydrastis canadensis, Xanthorhiza simplicissima, Phellodendron amurense, Coptis chinensis, Tinospora cordifolia, Argemone mexicana*, and *Eschscholzia californica* (Cicero A. F. G., Baggioni A. (2016) Berberine and Its Role in Chronic Disease. In: Gupta S., Prasad S., Aggarwal B. (eds) Anti-inflammatory Nutraceuticals and Chronic Diseases. Advances in Experimental Medicine and Biology, vol 928. Springer, Cham, the content of which is hereby incorporated by reference in its entirety).

Quercetin

Quercetin is a flavonoid and is attributed with pigmentation of flowers, fruits, and vegetables. Quercetin has antioxidant and free radical scavenging properties. The prevention and reduction of reactive oxygen species are therapeutically relevant to several disease states and conditions. (Anand David A V, Arulmoli R, Parasuraman S. Overviews of Biological Importance of Quercetin: A Bioactive Flavonoid. Pharmacogn Rev. 2016; 10(20):84-89. doi:10.4103/0973-7847.194044, the content of which is hereby incorporated by reference in its entirety).

Allocryptopine and Protopine

The isoquinoline alkaloids protopine (PRO) and allocryptopine (ALL) are found primarily in the plant families Fumariaceae, Papaveraceae, Berberidaceae and Ranunculaceae1,2,3,4,5. Both are also biologically active substances in human and veterinary phytopreparations from medicinal plants such as *Chelidonium majus* and *Macleaya cordata*6. PRO and ALL have many demonstrated biological activities, such as anti-thrombotic, anti-inflammatory7, anti-parasitic activity8, antimicrobial activity9, as well as hepatoprotective effects in animal models10. These biological activities of PRO and ALL are associated with its ability to inhibit K (ATP) channels11,12,13. Thus, the both alkaloids and associated plants have attracted increasing attention from pharmacologists due to their multiple biological effects. Huang, Y., Cheng, P., Zhang, Z. et al. Biotransformation and tissue distribution of protopine and allocryptopine and effects of Plume Poppy Total Alkaloid on liver drug-metabolizing enzymes. Sci Rep 8, 537 (2018). https://doi.org/10.1038/s41598-017-18816-7, the content of which is hereby incorporated by reference in its entirety).

Chelidonine, Chelamine, Alpha-Homochelidonine and Beta-Homochelidonine

Chelidonine is a major bioactive, isoquinoline alkaloid. Chelidonine has a few forms which are synthesized in a similar way and which are structurally alike, including: (+)-homochelidonine, and (+)-chelamine are tertiary benzo [c]phenanthridine alkaloids with partially hydrogenated B and C rings. They occur in a number of plant species of the family Papaveraceae. (Necas, M., Dostal, J., Kejnovska, I., Vorlickova, M., & Slavik, J. (2005). Molecular and crystal structures of (+)-homochelidonine, (+)-chelamine, and (−)-norchelidonine. Journal of Molecular Structure, 734(1-3), 1-6, the content of which is hereby incorporated by reference in its entirety).

Chelerythrine

Chelerythrine, a natural benzo [c] phenanthridine alkaloid existing in numerous plant species, is known to exert various biological activities, including antimicrobial, antifungal, anti-inflammatory and anticancer activities. In addition, CHE can inhibit protein kinase C and mitogen-activated protein kinase phosphatase-1 through various signaling pathways (Bo Hu et al. (2017). Chelerythrine Attenuates Renal Ischemia/Reperfusion-induced Myocardial Injury by Activating CSE/H2S via PKC/NF-κ3 Pathway in Diabetic Rats, Kidney and Blood Pressure Research, 42:379-388, the content of which is hereby incorporated by reference in its entirety).

Coptisine

Coptisine is a small-molecular isoquinoline alkaloid with diverse biological activity. Alone, coptisine has generally limited bioavailability and limited absorption. However, as presently disclosed, in combination with additional components described herein, the positive biological activity of coptisine is evident.

Magnoflorine

Magnoflorine is a quaternary benzylisoquinoline alkaloid of the aporphine structural subgroup which has been isolated from various species of the family Menispermaceae, such as *Pachygone ovata, Sinomenium acutum*, and *Cissampelos*

*pareira*. Magnoflorine is efficacious in antiviral, anti-inflammatory, and antimicrobial activity, for dispelling dampness, for removing toxicosis, and in detoxification (Tjong et al., 2011; Zhang et al., 2011; Cui et al., 2016; Friedemann et al., 2016; Kim et al., 2016)

Sparteine

Sparteine is an alkaloid extracted from plants such as *Cytisus scoparius*, the common broom or Scotch broom. Having several commercial and pharmaceutical applications, it has been identified as an antiarrhythmic agent and sodium channel blocker. (W. Marek Golebiewski and, Ian D. Spenser. Biosynthesis of the lupine alkaloids. II. Sparteine and lupanine. Canadian Journal of Chemistry, 1988, 66(7): 1734-1748, Chelidonic Acid, Malic Acid, Citric Acid Chelidonic acid, may be extracted from *Chelidonium majus* L., has many pharmacological effects, including mild analgesic and antimicrobial effects. (Dae-Seung Kim et al. The Therapeutic Effect of Chelidonic Acid on Ulcerative Colitis. Biological and Pharmaceutical Bulletin 2012 Volume 35 Issue 5 Pages 666-671). Malic acid is often used for pH adjustment. However, malic acid is presented as having additional benefits as a component of the present composition. In some embodiments, malic acid may be included in topical applications, or oral applications of the present composition. (Fiume Z. Final report on the safety assessment of Malic Acid and Sodium Malate. Int J Toxicol. 2001; 20 Suppl 1:47-55. doi:10.1080/109158101750300946, the content of which is hereby incorporated by reference in its entirety).

*Chelidonium Majus*

Constituents of *Chelidonium majus* may include several alkaloids such as coptisine methyl 2'-(7,8-dihydrosanguinarine-8-yl)acetate, allocryptopine, stylopine, protopine, norchelidonine, berberine, chelidonine, sanguinarine, chelerythrine, 8-hydroxydihydrosanguinarine, and Caffeic acid derivatives, such as caffeoylmalic acid, are also present. In some embodiments, the whole plant may be incorporated into the present composition or one or more constituents of *Chelidonium majus* may be extracted and incorporated into the present composition. (Cahlikova L., Opletal L., Kurfurst M., Macakova K., Kulhankova A., Host'alkova A., "Acetylcholinesterase and butyrylcholinesterase inhibitory compounds from *Chelidonium majus* (Papaveraceae)." Natural Product Communications. 5 (11) (pp 1751-1754), 2010. Date of Publication: 2010).

Turmeric Curcumin

Turmeric is a spice that has received much interest from both the medical/scientific worlds as well as from the culinary world. Turmeric is a rhizomatous herbaceous perennial plant (*Curcuma longa*) of the ginger family. Curcumin (1,7-bis(4-hydroxy-3-methoxyphenyl)-1,6-heptadiene-3,5-dione), also called diferuloylmethane, is the main natural polyphenol found in the rhizome of *Curcuma longa* (turmeric) and in others *Curcuma*. Curcumin, a polyphenol, has been shown to target multiple signaling molecules while also demonstrating activity at the cellular level, which has helped to support its multiple health benefits. It has been shown to benefit inflammatory conditions, metabolic syndrome, pain, and to help in the management of inflammatory and degenerative eye conditions. In addition, it has been shown to benefit the kidneys. While there appear to be countless therapeutic benefits to curcumin supplementation, most of these benefits are due to its antioxidant and anti-inflammatory effects. (Hewlings S J, Kalman D S. Curcumin: A Review of Its' Effects on Human Health. Foods. 2017; 6(10):92. Published 2017 Oct. 22. doi:10.3390/foods6100092). In some embodiments, turmeric may refer to curcumin.

Beetroot

Beetroot consists of multiple biologically active phytochemicals including betalains (e.g., betacyanins and betaxanthins), flavonoids, polyphenols, Saponins and inorganic Nitrate (NO3); it is also a rich source of diverse minerals such as potassium, sodium, phosphorous, calcium, magnesium, copper, iron, zinc and manganese. (Mirmiran P, Houshialsadat Z, Gaeini Z, Bahadoran Z, Azizi F. Functional properties of beetroot (*Beta vulgaris*) in management of cardio-metabolic diseases. Nutr Metab (Lond). 2020; 17:3. Published 2020 Jan. 7. doi:10.1186/s12986-019-0421-0, the content of which is hereby incorporated by reference in its entirety).

Chondroitin

Chondroitin sulfate is a major component of the extracellular matrix of many connective tissues, including cartilage, bone, skin, ligaments and tendons. CS, as a natural component of the extracellular matrix, is a sulfated glycosaminoglycan composed of a long unbranched polysaccharide chain with a repeating disaccharide structure of N-acetylgalactosamine and glucuronic acid. Most of the N-acetylgalactosamine residues are sulfated, particularly in the 4- and 6-position, making chondroitin sulfate a strongly charged polyanion. Chondroitin sulfate is responsible for many of the important biomechanical properties of cartilage, such as resistance and elasticity. Its high content in the aggrecan plays a major role in allowing cartilage to resist pressure stresses during various loading conditions. (Henrotin Y, Mathy M, Sanchez C, Lambert C. Chondroitin sulfate in the treatment of osteoarthritis: from in vitro studies to clinical recommendations. Ther Adv Musculoskelet Dis. 2010; 2(6):335-348. doi:10.1177/1759720X10383076, the content of which is hereby incorporated by reference in its entirety).

Glucosamine

Glucosamine is an amino sugar that is essential for the biosynthesis of glycosylated proteins and lipids. It is a major constituent of extracellular matrix macromolecules such as glycosaminoglycans, glycolipids and glycoproteins in its acetylated form. It is present in high quantities in articular cartilage, intervertebral disc and synovial fluid. Glucosamine can also be extracted from the chitosan and chitin exoskeleton of crustaceans such as shellfish and may be stabilized as a salt, glucosamine hydrochloride or glucosamine sulfate for oral administration. (Henrotin Y, Mobasheri A, Marty M. Is there any scientific evidence for the use of glucosamine in the management of human osteoarthritis?. Arthritis Res Ther. 2012; 14(1):201. Published 2012 Jan. 30. doi:10.1186/ar3657, the content of which is hereby incorporated by reference in its entirety).

L-Carnitine 1-carnitine is a low-molecular, nitrogenous compound, the main role of which is transporting long-chain fatty acids from the cytoplasm into the mitochondrial matrix. It also possesses anti-inflammatory properties. 1-carnitine attenuates inflammatory changes in various experimental models: aging, liver fibrosis or cancer cachexia. (Sawicka, A. K.; Hartmane, D.; Lipinska, P.; Wojtowicz, E.; Lysiak-Szydlowska, W.; Olek, R. A. 1-Carnitine Supplementation in Older Women. A Pilot Study on Aging Skeletal Muscle Mass and Function. Nutrients 2018, 10, 255, the content of which is hereby incorporated by reference in its entirety).

Apigenin *Chrysanthemum morifolium* Extract

Apigenin, chemically known as 4',5,7-trihydroxyflavone is a yellow crystalline powder belonging to the flavone class, that is the aglycone of several naturally occurring glycosides. It is insoluble in water but soluble in organic solvents. Numerous pharmacological activities, including anti-inflammatory, anti-toxicant, anti-cancer, etc., are attributed to apigenin. Research has shown that apigenin has numerous molecular targets involved in inflammation. (Fahad Ali, Rahul, Falaq Naz, Smita Jyoti & Yasir Hasan Siddique (2017) Health functionality of apigenin: A review, International Journal of Food Properties, 20:6, 1197-1238, DOI: 10.1080/10942912.2016.1207188) (Li L P, Wu X D, Chen Z J, et al. Interspecies difference of luteolin and apigenin after oral administration of *Chrysanthemum morifolium* extract and prediction of human pharmacokinetics. Pharmazie. 2013; 68(3):195-200) (Yuxiao Wang et al. Extraction, Purification, and Hydrolysis Behavior of Apigenin-7-O-Glucoside from *Chrysanthemum Morifolium* Tea. Molecules 2018, 23, 2933; doi:10.3390).

Sanguinarine

Sanguinarine is generally accepted as a toxic alkaloid contained within plant species such as *Sanguinaria canadensis*. Sanguinarine interacts with DNA via intercalation, having a binding co-efficient comparable to the anthracycline agents daunorubicin and doxorubicin. Its binding impairs DNA polymerase inducing DNA strand breaks and cell death. Its cytotoxic properties are advantageous as an anti-tumoral or anti-cancer agent. In some embodiments, sanguinarine is extracted of removed for interacting with other alkaloids that may or may not be extracted from the same plant. However, in alternative embodiments, sanguinarine is selectively incorporated into the composition for specific cytotoxic applications. For example, the composition may comprise sanguinarine for topical applications and targeted administration to visible tumors. (Croaker A, King G J, Pyne J H, Anoopkumar-Dukie S, Liu L. *Sanguinaria canadensis*: Traditional Medicine, Phytochemical Composition, Biological Activities and Current Uses. Int J Mol Sci. 2016; 17(9):1414. Published 2016 Aug. 27. doi:10.3390/ijms17091414)

Hypromellose and Silica

Hypermellose may provide a non-limiting example of a component included in the present composition for increasing or enhancing the delivery of an orally administered dose of the composition Hypromellose, short for hydroxypropyl methylcellulose, is a semisynthetic, inert, viscoelastic polymer used as eye drops, as well as an excipient and controlled-delivery component in oral medicaments, found in a variety of commercial products. As a food additive, hypromellose is an emulsifier, thickening and suspending agent, and an alternative to animal gelatin. (Williams R O, Sykora M A, Mahaguna V (2001). "Method to recover a lipophilic drug from hydroxypropyl methylcellulose matrix tablets". AAPS PharmSciTech. 2 (2): 29-37) (Ali Nokhodchi; Shaista Raja; Pryia Patel; Kofi Asare-Addo (November 2012). "The Role of Oral Controlled Release Matrix Tablets in Drug Delivery Systems". Bioimpact. 2 (4): 175-87).

Formulations

In some embodiments, the composition may be administered systemically or locally, usually by oral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose to be used does can depend upon various conditions, and there may be cases wherein doses lower than or greater than the ranges specified above are used.

In some embodiments, the composition comprises each included component by weight depending upon, for example, age, body weight, symptom, the desired therapeutic effect, the route of administration, and the duration of the treatment. The composition may comprise each component at a weight generally from at least about 0.01 mg to 1000 mg or beyond. Specific examples of particular amounts contemplated for each component include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose to be used does can depend upon various conditions, and there may be cases wherein doses lower than or greater than the ranges specified above are used. Each component included in the composition may be the same weight as one or more other included components. Alternatively, one or all components included in the composition may be included at a different weight.

In some embodiments, the composition is prepared as a solid an orally administered via a capsule containing the solid composition. Each capsule contains a quantity of the total composition and the administration is based on weight of the subject consuming the capsule.

In some embodiments, the subject receiving administration of the composition is identified having a disease or condition. In some embodiments, the disease or condition is aging.

In some embodiments, the subject receiving the administration of the composition is a mammal. A non-limiting example of administration dosing provides that the mammal may be a canine whereby the composition is administered as a capsule based on the weight of the mammal. For example, a canine weighing between 5-14 pounds will be administered 1 capsule; weighing between 15-29 pounds will be administered 2 capsules; weighing between 30-59 pounds will be administered 3 capsules; and weighing 60 pounds or greater will be administered 3 capsules or more.

In some embodiments, the composition comprises the at least one alkaloid combined with one or more additional components in a ratio with one another by weight. The inclusion of a particular component of the present composition may be based on the specific application of the composition as it relates to a desired therapeutic effect.

In some embodiments, the composition is administered to a subject having a condition affecting one or more joints. The condition affecting one or more joints may be due to an injury, auto-immune disease such as arthritis, or inflammation. The one or more joint may be synarthroses, amphiarthroses, or diarthroses. In such a subject the composition comprises berberine, beetroot, cinnamon, chondroitin and glucosamine in a capsule. A non-limiting example of the weight of each component for the treatment of a condition affecting one or more joints may be at least 50 mg of berberine, 50 mg of beetroot, 20 mg of cinnamon, 25 mg of chondroitin and 25 mg of glucosamine in a capsule. The ratio of these component may be maintained at a higher or lower total composition weight.

Another non-limiting example of the weight of each component for the treatment of a condition affecting one or more joints may be at least 100 mg of berberine (berberine hydrochloride), 50 mg of chondroitin sulfate, 50 mg of glucosamine sulfate (potassium salt), 100 mg of beetroot powder, and 40 mg of turmeric in a capsule. The ratio of these component may be maintained at a higher or lower total composition weight.

Composition for the Treatment of Age-Related Diseases or Conditions

Some embodiments disclosed herein provide a composition for the treatment or prevention of age-related diseases or conditions. In some embodiments, the composition is therapeutically effective in treating or preventing age-related diseases or conditions. For example, a subject over the age of 35 may be identified has having increased intrinsic production of reactive oxygen species. Subjective factors in identifying age-related conditions may include increased fatigue, digestion dysfunction, decreased skin integrity, decreased energy, and decreased bone integrity. In such a subject, the composition comprises berberine, quercetin, apigenin, *Chrysanthemum morifolium* extract (CME), and l-carnitine. In other embodiments for the treatment and prevention of age-related conditions, the composition may be formulated for topical application and further comprise malic-acid. A non-limiting example of the weight of each component of the composition therapeutically effective in treating or preventing age-related diseases or conditions may be at least 75 mg of berberine, 37.5 mg of quercetin, 6.25 mg of apigenin CME, and 6.25 mg of l-carnitine in a capsule. The ratio of these component may be maintained at a higher or lower total composition weight.

Composition for the Treatment of Cancer

Some embodiments disclosed herein provide a composition for the treatment or prevention of cancer. In some embodiments, the composition is administered to a subject having cancer or at risk of developing cancer. The subject may be identified through evaluation of one or more factors generally accepted and required for the diagnosis or increased risk of cancer. In such subject, the composition comprises at least berberine, chelerythrine, beetroot and turmeric.

Another non-limiting example of the weight of each component for the treatment or prevention of cancer may be at least 100 mg of berberine, 100 mg of beetroot, 1 mg of chelerythrine, and 40 mg of turmeric in a capsule. The ratio of these component may be maintained at a higher or lower total composition weight.

Another non-limiting example of the weight of each component for the treatment or prevention of cancer may be at least 50 mg of berberine, 50 mg of beetroot, 40 mg of cinnamon in a capsule and at least 12.5 mg of one or more of the following: allocryptopine, chelamine, chelidonine, chelerythrine, coptisine, magnoflorine, protopine, sparteine, alpha-homochelidonine, beta-homochelidonine, chelidonic acid, citric acid, and *Chelidoninium majus*. The ratio of these component may be maintained at a higher or lower total composition weight.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumor, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Composition for the Treatment of Joint Damage

In some embodiments, the composition is administered to a subject having a condition affecting one or more joints. The condition affecting one or more joints may be due to an injury, auto-immune disease such as arthritis, or inflammation. The one or more joint may be synarthroses, amphiarthroses, or diarthroses. In such a subject the composition comprises berberine, beetroot, cinnamon, chondroitin and glucosamine in a capsule. A non-limiting example of the weight of each component for the treatment of a condition affecting one or more joints may be at least 50 mg of berberine, 50 mg of beetroot, 20 mg of cinnamon, 25 mg of chondroitin and 25 mg of glucosamine in a capsule. The ratio of these component may be maintained at a higher or lower total composition weight.

Another non-limiting example of the weight of each component for the treatment of a condition affecting one or more joints may be at least 100 mg of berberine (berberine hydrochloride), 50 mg of chondroitin sulfate, 50 mg of glucosamine sulfate (potassium salt), 100 mg of beetroot powder, and 40 mg of turmeric in a capsule. The ratio of these component may be maintained at a higher or lower total composition weight.

In some embodiments, the composition may be administered proactively as a maintenance for proper and efficient biological functions. In such an example of administration, the composition may have 100 mg of berberine HCl, 1 mg of chelerythine, 100 mg of beet root powder (*Beta Vulgaris*), 40 mg of turmeric root powder (*Curcuma Longa*), in a gelatin capsule also having 10 mg of silicon dioxide, 39 mg of rice flour, and 10 mg of magnesium stearate.

Routes of Administration

The composition can be administered in the form of, for example, solid compositions, liquid compositions or other compositions for oral administration, topical administration, injections, liniments or suppositories for parenteral administration.

Solid compositions for oral administration include compressed tablets, pills, capsules, dispersible powders and granules. Capsules include hard capsules and soft capsules. In such solid compositions, the composition may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the composition is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Liquid compositions for topical administration include pharmaceutically acceptable solutions, suspensions, or emulsions suitable for topical application to skin or hair. For example, the composition may be combined with a commercially available lotion, salve, ointment, shampoo, or cream and applied to outer layers of tissue of an organism.

Injections for parenteral administration include solutions, suspensions, emulsions and solids which are dissolved or suspended. For injections, the composition can be dissolved, suspended and emulsified in a solvent. The solvents include, for example, distilled water for injection, physiological salt solution, vegetable oil, propylene glycol, polyethylene glycol, alcohol such as ethanol, or a mixture thereof. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition comprising a therapeutically effective amount of at least
   a. one alkaloid selected from the group consisting essentially of berberine, allocryptopine, alpha-homochelidonine, beta-homochelidonine, chelidonine, chelerythrine, coptisine, magnoflorine, protopine, sparteine, chelamine, and sanguinaria,
b. at least 50 mg of beetroot,
c. and at least one component selected from the group consisting essentially of allocryptopine, chelamine, chelidonine, chelerythrine, coptisine, magnoflorine, protopine, sparteine, alpha-homochelidonine, beta-homochelidonine, chelidonic acid, malic acid, and citric acid, wherein the composition is configured to be administered to a subject known to have arthritis.

2. The composition of claim 1 wherein the composition further comprises one or more non-alkaloid components.

3. The composition of claim 2, wherein at least one of the one or more non-alkaloid components is a polyphenol.

4. The composition of claim 1, wherein the at least one alkaloid is 50 mg of berberine.

5. The composition of claim 1, wherein the composition is a solid and wherein the composition is orally administered via a capsule.

6. The composition of claim 1, wherein the composition comprises at least 50 mg of berberine, 50 mg of beetroot, 20 mg of cinnamon, 25 mg of chondroitin and 25 mg of glucosamine.

7. The composition of claim 1, wherein the composition comprises at least 100 mg of berberine, 50 mg of chondroitin, 50 mg of glucosamine, 100 mg of beetroot powder, and 40 mg of turmeric.

8. The composition of claim 1, wherein the composition comprises at least 100 mg of berberine, 100 mg of beetroot, 1 mg of chelerythrine, and 40 mg of turmeric.

9. The composition of claim 1, wherein the at least one alkaloid is derived and extracted from a plant species.

10. The composition of claim 1, wherein at least one of the one or more non-alkaloid components is an excipient.

11. The composition of claim 1, wherein the one or more non-alkaloid components increases bioavailability of the composition.

12. The composition of claim 1, wherein the composition is a lotion.

13. The composition of claim 1, wherein the at least one alkaloid consists of 50 mg berberine and chelerythrine.

14. The composition of claim 1, wherein the one or more non-alkaloid components are chondroitin and glucosamine.

15. The composition of claim 1, wherein the non-alkaloid component is at least curcumin.

\* \* \* \* \*